United States Patent [19]

Pagani et al.

[11] Patent Number: 5,660,801
[45] Date of Patent: Aug. 26, 1997

[54] PROCESS AND APPARATUS FOR THE REVAMPING OF UREA SYNTHESIS PLANTS CONSISTING OF A STRIPPER WITH AMMONIA

[75] Inventors: Giorgio Pagani, Milan, Italy; Umberto Zardi, Breganzona, Switzerland

[73] Assignee: Urea Casale S.A., Switzerland

[21] Appl. No.: 458,123

[22] Filed: Jun. 2, 1995

Related U.S. Application Data

[62] Division of Ser. No. 987,127, Dec. 8, 1992.

[30] Foreign Application Priority Data

Nov. 19, 1992 [CH] Switzerland ............... 03544/92

[51] Int. Cl.$^6$ ...................................... B01J 8/04
[52] U.S. Cl. .................. 422/189; 422/187; 422/188; 422/196; 564/67
[58] Field of Search .................. 422/187, 188, 422/189, 196; 564/67, 69, 70, 71, 72, 63

[56] References Cited

U.S. PATENT DOCUMENTS

| | | | |
|---|---|---|---|
| 3,470,247 | 9/1969 | Guadalupe | 564/72 |
| 4,670,588 | 6/1987 | Zardi | 564/72 |
| 4,801,746 | 1/1989 | Baenens | 546/72 |

FOREIGN PATENT DOCUMENTS 0 479 103 A1  4/1992  European Pat. Off. .

Primary Examiner—Christopher Kim
Attorney, Agent, or Firm—Ostrolenk, Faber, Gerb & Soffen, LLP

[57] ABSTRACT

Process and apparatus for the revamping of urea production plants for the synthesis of ammonia (NH3) and carbon dioxide, with a stripping section with NH3, in which the process carries out with differentiated yields, a majority reaction a) between highly pure reagents and a reaction b) between less pure substantially recycled reagents. According to the invention, the urea solution is now fed upstream the stripping section and a reactor with heat removal is utilized. Advantageously, the production capacity of the existing reactor is reduced, with respect to the projected one, in a quantity of 35% to 5%, preferably from 20% to 10%, in favor of the capacity of the "once-through" reactor.

3 Claims, 3 Drawing Sheets

PROCESS AND APPARATUS FOR THE REVAMPING OF UREA SYNTHESIS PLANTS CONSISTING OF A STRIPPER WITH AMMONIA

This is a division of application Ser. No. 07/987,127, filed Dec. 8, 1992.

This invention concerns a process for the industrial synthesis of urea, by reacting ammonia (NH3) and carbon dioxide (CO2), in at least one reaction space at very high pressures and temperatures, and by recycling at least partially the non-reacted products obtained in a recovery section, in which the following actions take place: a) a synthesis reaction between highly pure reagents and b) a synthesis reaction between less pure reagents substantially recycled from said recovery section.

A highly innovative and novel process of this kind is described in U.S. Pat. No. 5,403,956 by the Applicant.

A very advantageous invention, the process according to above mentioned U.S. Patent, is based on an original combination of two synthesis reactors placed in parallel, one operating according to the so-called "once through" technology (i.e. fed by pure regents without recycle water) with high yield, and a second reactor according to the total recycle technology (i.e. fed not only by pure reagents, but also with an aqueous recycle solution) with high yield.

In this manner it is possible to obtain very high global conversion yields of CO2 into urea, much higher than those obtainable with conventional processes. In said U.S. Pat. No. 5,403,956, an example is shown of the revamping of a urea plant based on the urea production process with NH3 stripping (selfstripping).

Continuing their research and experiments, the Applicants were able to develop a new revamping process applicable to existing Ammonia Stripping Urea Plants consisting of a stripping stage with NH3, with the aim of notably increasing the capacity and reducing the energy consumption. This new process is to be considered an original variation of the invention cited in the said U.S. Patent.

In particular, in FIG. 3 of U.S. Pat. No. 5,403,956, a stripping plant with NH3 was shown revamped with the addition of a high yield reactor R in parallel to the "once through" reactor (in particular of the Vulcan type), the urea solution of which was sent directly downstream to the existing HP stripper. It should be noted that said reactor was of adiabatic type, in the sense that all the reaction heat developed from the formation of ammonium carbamate and subsequently dehydrated to urea, was needed to make the reactants reach the necessary operating temperature of the reactor.

The aim of this invention is now to provide an improved process that consents the obtainment of average high conversion yields, reduction of investment and operation costs, better plant exploitation and more ample overload margins of the existing equipment, and considerable plant debottlenecking.

This and other aims are reached with a kind of process, according to the said U.S. Pat. No. 5,403,956, characterized now by the fact that from the parallel reactor ("once through") at least a part of the reaction heat is removed, and the relevant urea solution is sent upstream to the existing stripper. Very advantageously, the production capacity of the existing reactor is reduced with respect to the projected one, and the capacity of the "once through" reactor is increased correspondingly.

BRIEF DESCRIPTION OF THE DRAWING

Various aspects and advantages of the invention will be better illustrated by the description of the attached drawings, in which:

In order to clarify the idea better, FIG. 1 illustrates the conventional scheme of an isobaric stripping process with a synthesis reactor (stripping with NH3, selfstripping) (FIG. 1).

In the stripper (S) a large part of the carbamate contained in the urea solution exiting from the reactor (R) and part of the free NH3 present are stripped and recycled to the reactor, while a urea solution (SU) is obtained exiting from the stripper (S) having a relatively low residual Co2 content (5–7% weight), and a relatively high NH3 content (22–25% weight). This solution (SU) is treated in one medium pressure stage (SMP) where it is distilled at 18–20 bar and the vapors obtained are sent to a rectifying column (CR) that consents to obtain highly pure NH3 (NEP) at the top, and carbamate solution (SC) at the bottom.

The highly pure NH3, previous to condensation, is mixed together with the NH3 feed (NA) and is pumped (Pump P) to reactor (R), and the same process is carried out with the carbamate solution (Pump P').

The main technical characteristics of the isobaric ammonia stripping process can be summarized as follows:

synthesis pressure: ~150 bar

NH3/CO2 mol in the reactor: ~3.2–3.4

H20/CO2 mol in the reactor: ~0.6–0.8 temperature of the reactor: 190° C.

yield: ~62–63% steam consumption: ~900 kg/MT urea

The above mentioned values are quite consolidated and great improvements to the process do not seem possible.

Figure 1:
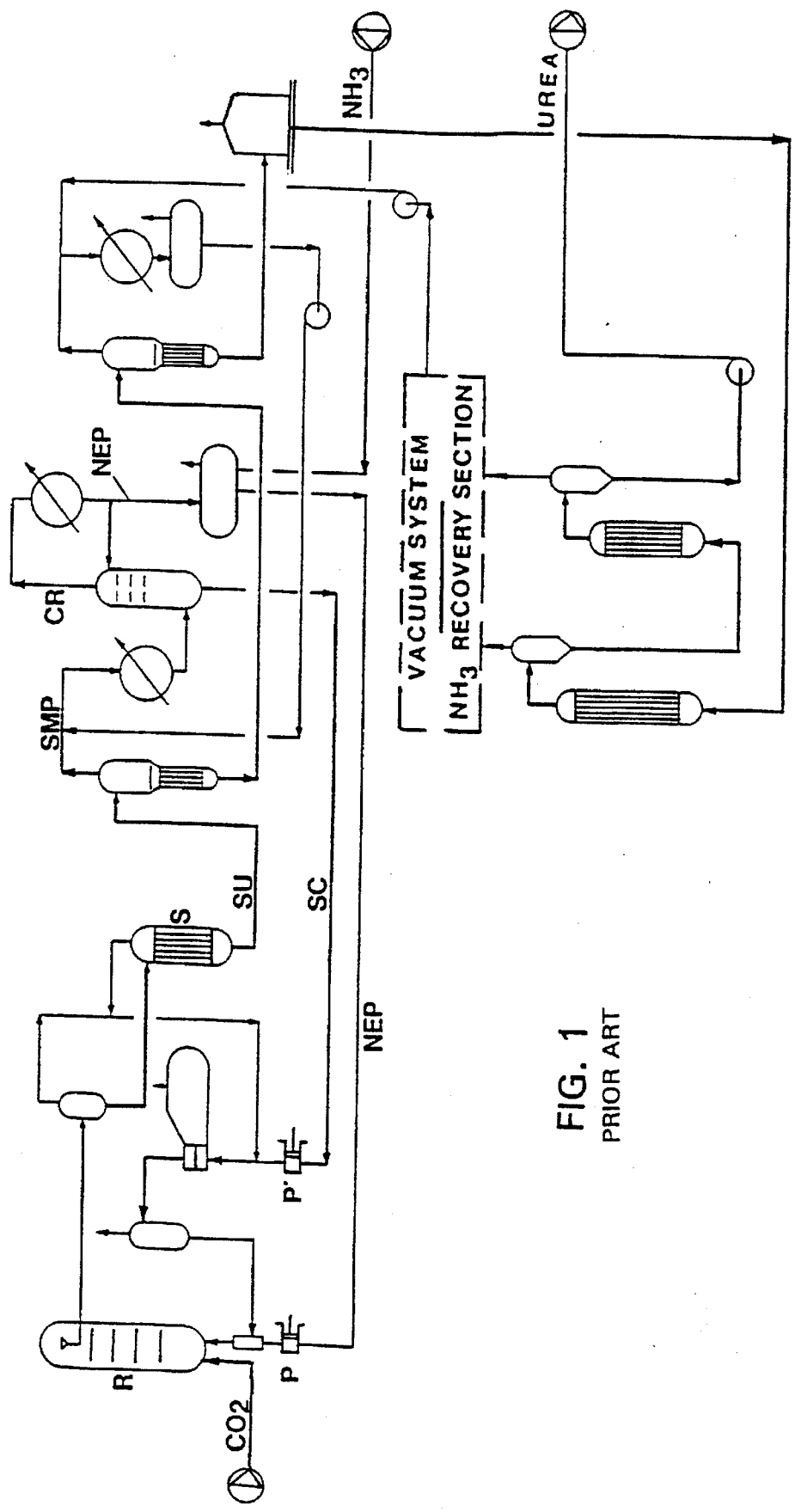
FIG. 1 is a conventional scheme of an ammonia stripping process.
Figure 2:
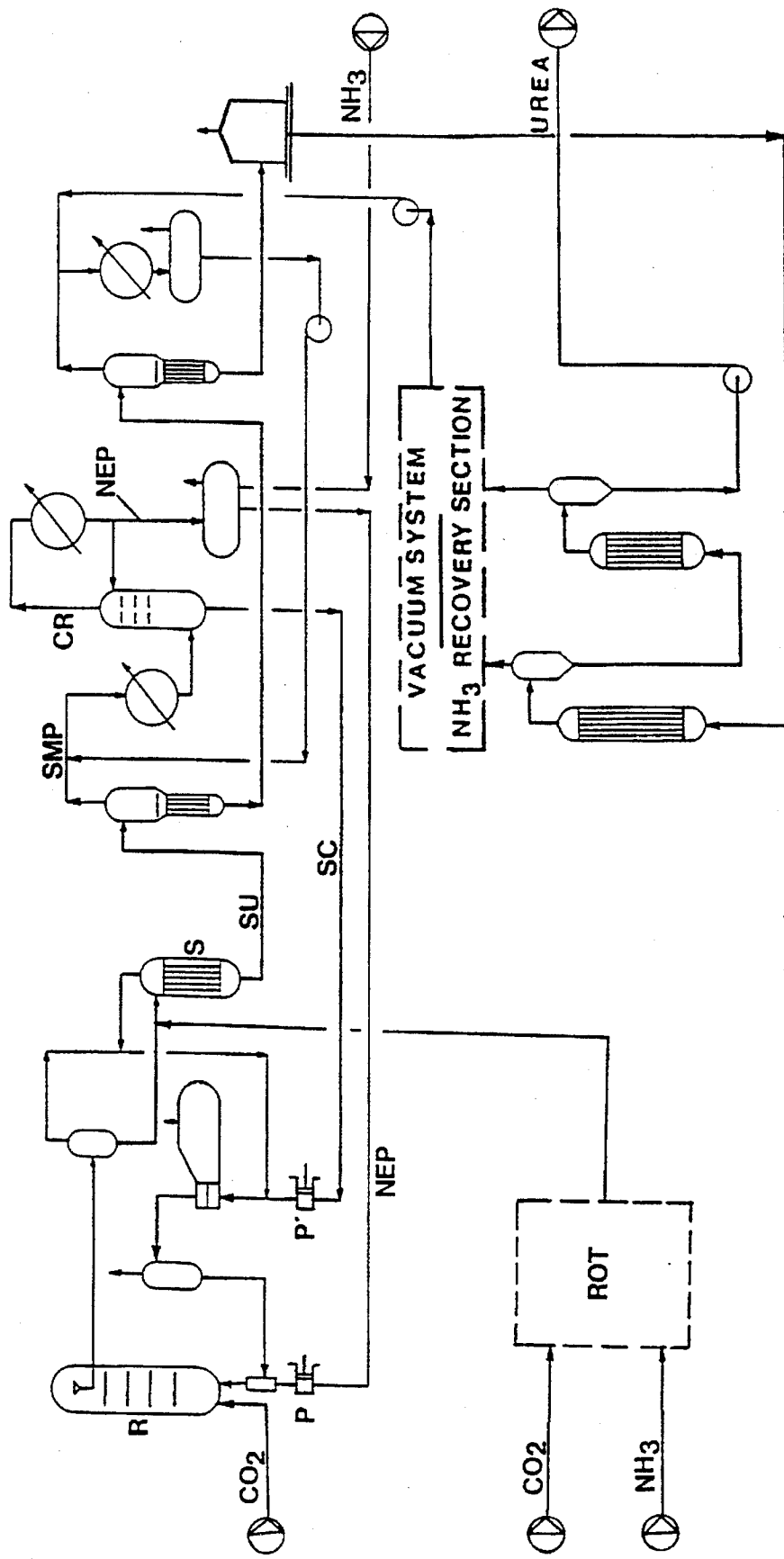
FIG. 2 is a scheme resulting from the application of the invention of said conventional type plant as shown in FIG. 1.

In FIG. 2 the same process diagram as in FIG. 1 is shown, except modified according to this invention, i.e. with the addition of a parallel reactor of the "once through" type ROT, the urea solution of which is sent to the line upstream the existing stripper, may be a reactor of adiabatic type or with partial removal of the reaction heat.

In any event, in the preferred embodiment of this invention the use of the "once through" reactor ROT with partial reaction heat removal results particularly suitable for the revamping of stripping plants with NH3.

In fact it was found that it is possible to revamp in an even more efficient manner plants of the types as in FIG. 1, still within the limits of the process at differentiated yields, according to said U.S. Patent, by foreseeing as parallel reactor, a "once through" type reactor with partial removal of the reaction heat and by sending the urea solution not downstream, but upstream the existing stripper.

Figure 3:
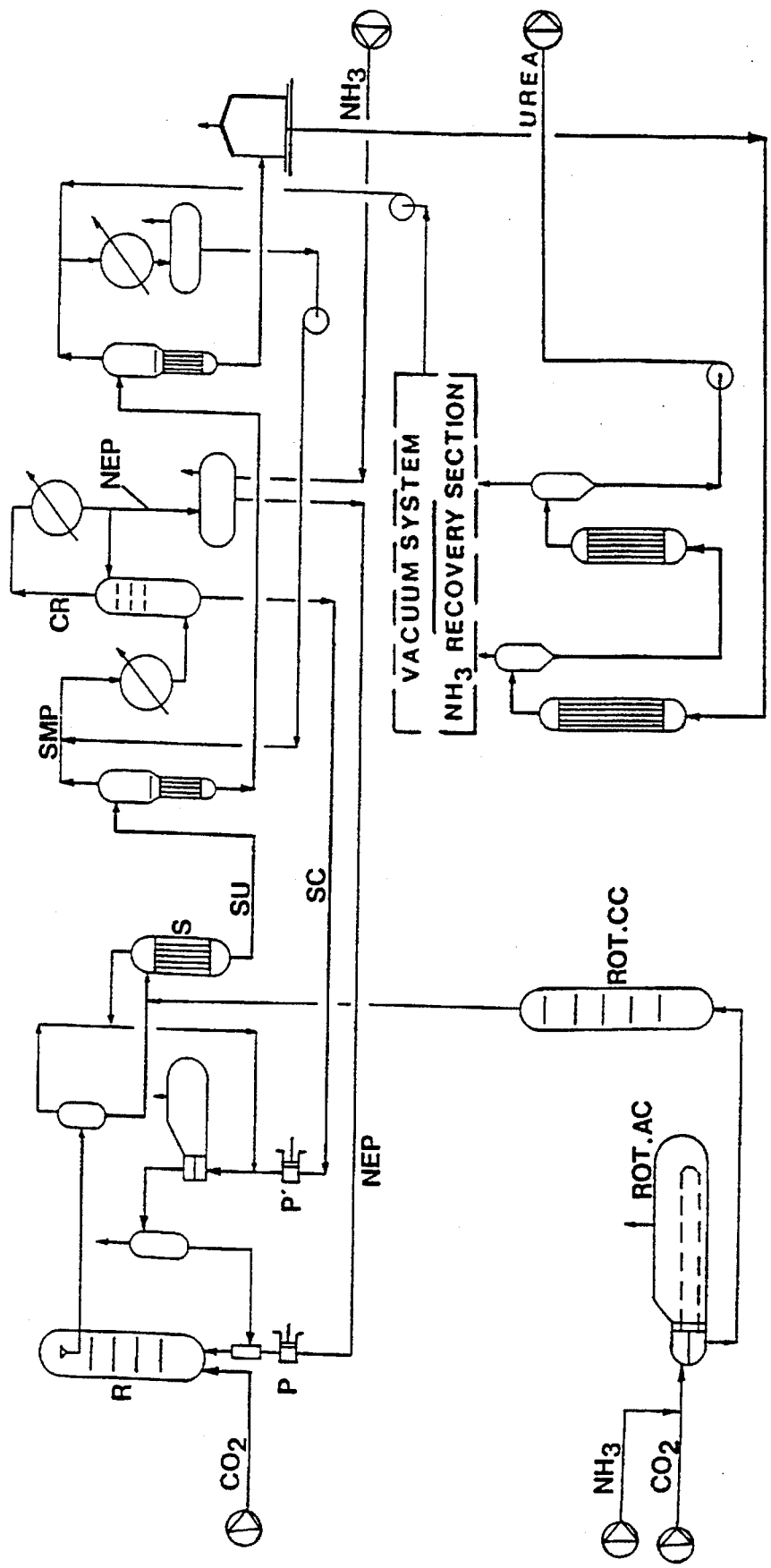
FIG. 3 is a scheme with a "once through" reactor in two pieces.

In FIG. 3 a scheme of a stripping plant with NH3 is shown, with the addition of a parallel reactor of the "once through" type ROT, subdivided into two parts:

"primary reactor" with reaction heat removal ROT.AC;

"secondary reactor" of conventional type ROT.CC.

In general the ROT.AC is a reactor known as a "Kettle" type reactor.

It should be noted that similar reactors have been built in various urea solution production plants by the American Company Weatherly.

The use of these reactors for the revamping of said plants is particularly interesting, because they can be fed by the existing ammonia pumps that have a delivery pressure higher than the operating pressure of the reactors (260 bar against 240 bar).

This fact consents a notable reduction of investment cost. Another interesting aspect of this invention is that it is possible, by evenly distributing the load on the existing reactor and on the "once through" one, thus obtaining an average conversion yield notably higher than the typical one of the original project, and this fact consents the acquisition of more ample overloading margins for the key plant equipment, such as the stripper, carbamate condenser, MP distiller and considerable debottlenecking of the plant itself. In an advantageous way, the production capacity of the existing plant is reduced in favor of the "once through" reactor, to any quantities inferior by 40%, from, for example, 35% to 5%, pefferably below 30%, and better yet if in the order of 20–10%. this signifies that the production in the "once through" reactor increases correspondingly 35–5%, typically 20–10%.

In order to better clarify these concepts, an example of the revamping of an existing 1500 MTD urea stripping plant with NH3 is given (of course, in a not limitative way).

The aim of the revamping is to increase the capacity of the synthesis sections and distillation at 145 bar, 18 bar, and 4 bar (HP, MP, LP) by adding a new reactor of the "once through" type in parallel to the existing one.

The new capacity shall be 1500×1.5=2250 MTD urea.

As already mentioned, it is possible to maintain or to reduce the thermal load of the main equipment (excluding the vacuum section), by evenly distributing the load between the two reactors. In the case herein considered, the optimal distribution is as follows:

| Existing reactor | 1350 MTD urea |
| New reactor | 900 MTD urea |
| TOTAL | 2250 MTD urea |

The operating conditions of the reactors are:

a) Reference Case

Existing reactor:

| capacity | 1500 MTD |
| NH3/CO2 mol | 3.6 |
| H20/CO2 mol | 0.68 |
| Yield | 62% |
| P = 145 bar T = 190° C. | | b) New Conditions b.1 Existing Reactor:

| Capacity | 1350 MTD |

-continued

| NH3/CO2 mol | 3.6 |
| H20/CO2 mol | 0.75 |
| Yield | 61% |
| P = 145 bar T = 190° C. | | b.2. "Once Through" Reactor

| Capacity | 900 MTD |
| NH3/CO2 mol | 3.6 |
| H20/CO2 mol | 0 |
| Yield | 75% |
| P = 242 bar T = 193° C. | |

The weighed yield of the two reactors operating in parallel is:

$$\frac{1350 \times 61 + 900 \times 75}{2250} = 66.6\%$$

i.e. 4.6 percentage points in respect to the reference case. This corresponds to a minor specific steam consumption of 100–130 Kg/MT urea, despite the increase of capacity.

It results that the capacity of the existing stripper, MP and LP distillers and carbamate condenser are adequate also for the new operating conditions.

We claim:

1. A urea production plant comprising:

a first urea synthesis reactor;

a carbamate condenser upstream of said first reactor;

means for recycling a carbamate solution from said carbamate condenser to said first reactor;

a second urea synthesis reactor of the once-through type comprising means for partially removing the reaction heat and having higher efficiency yield than said first reactor and said second reactor being connected in parallel with said first reactor;

an ammonia stripping section, downstream of said first reactor and said second reactor, for separating a vapor phase including unreacted ammonia and carbon dioxide from an aqueous urea solution obtained from both the first and the second urea synthesis reactors;

a conduit for recycling said vapor phase from said ammonia stripping section to said carbamate condenser; and a conduit for connecting said second urea synthesis reactor to, and upstream of, said ammonia stripping section.

2. The plant of claim 1, wherein said second urea synthesis reactor comprises a primary section and a secondary section, and wherein said means for partially removing the reaction heat is located in said primary section.

3. A plant according to claim 2, wherein said primary section comprises a kettle reactor.

* * * * *